(12) United States Patent
Kohler

(10) Patent No.: US 8,674,322 B2
(45) Date of Patent: Mar. 18, 2014

(54) STERILIZING DEVICE AND A METHOD FOR STERILIZING OF FLUIDS

(76) Inventor: Guido Kohler, Kriens (CH)

(*) Notice: Subject to any disclaimer, the term of this patent is extended or adjusted under 35 U.S.C. 154(b) by 1331 days.

(21) Appl. No.: 11/578,856

(22) PCT Filed: Apr. 20, 2005

(86) PCT No.: PCT/CH2005/000218
§ 371 (c)(1),
(2), (4) Date: Nov. 17, 2006

(87) PCT Pub. No.: WO2005/102401
PCT Pub. Date: Nov. 3, 2005

(65) Prior Publication Data
US 2008/0095661 A1    Apr. 24, 2008

Related U.S. Application Data

(60) Provisional application No. 60/563,473, filed on Apr. 20, 2004.

(51) Int. Cl.
*G01N 23/10* (2006.01)
(52) U.S. Cl.
USPC ............. 250/436; 422/24; 422/119; 422/128; 210/748.1
(58) Field of Classification Search
USPC ................ 422/20, 22–24, 119, 128; 250/436; 210/748.1
See application file for complete search history.

(56) References Cited

U.S. PATENT DOCUMENTS

| 4,101,777 A | * | 7/1978 | Reid ............................ 250/436 |
| 4,454,766 A | | 6/1984 | Reinhold et al. |
| 5,709,799 A | * | 1/1998 | Engelhard .................. 210/748.1 |
| 5,997,812 A | * | 12/1999 | Burnham et al. ............... 422/24 |
| 6,071,473 A | * | 6/2000 | Darwin .......................... 422/20 |
| 6,201,355 B1 | * | 3/2001 | Morgan et al. ................ 250/436 |

(Continued)

FOREIGN PATENT DOCUMENTS

| CH | 477 825 | 9/1969 |
| JP | 2003-502153 | 1/2003 |

(Continued)

OTHER PUBLICATIONS

Official Office Action issued by the Japanese Patent Office, 2010.

*Primary Examiner* — Walter D Griffin
*Assistant Examiner* — Timothy Cleveland
(74) *Attorney, Agent, or Firm* — Davis&Bujold, PLLC; Michael J. Bujold

(57) ABSTRACT

The invention is directed to an improved sterilizing device (1) for sterilizing of a fluid by UV-radiation. The sterilizing device (1) has a modular setup with at least one flange (2, 3), an inner and an outer tube (4, 5) and comprises at least one UV-lamp (16) for emitting UV-radiation. A lamp tag (32) attached to or incorporated in the at least one UV-lamp (16) comprises information regarding the UV-lamp (16). The lamp tag (32) is interconnected with a lamp sensor unit (18) and/or a control unit (19) and may comprise sensors to control the sterilizing process.

26 Claims, 8 Drawing Sheets

(56) References Cited

U.S. PATENT DOCUMENTS

| | | |
|---|---|---|
| 6,402,926 B1 | 6/2002 | Sekhar et al. |
| 6,451,202 B1 | 9/2002 | Kuennen et al. |
| 6,646,269 B1 * | 11/2003 | Traubenberg et al. ........ 250/436 |
| 6,693,397 B2 | 2/2004 | Handa et al. |
| 6,706,170 B1 | 3/2004 | De Baat Doelman |
| 2002/0060177 A1 * | 5/2002 | Conrad ........................ 210/203 |
| 2002/0189986 A1 | 12/2002 | Kuennen et al. |
| 2005/0205658 A1 * | 9/2005 | Baker et al. ................... 235/375 |
| 2008/0224066 A1 * | 9/2008 | Nolen et al. .................. 250/436 |

FOREIGN PATENT DOCUMENTS

| | | |
|---|---|---|
| WO | WO-99/27972 | 6/1999 |
| WO | WO 00/14018 | 3/2000 |
| WO | WO 00/78678 | 12/2000 |

* cited by examiner

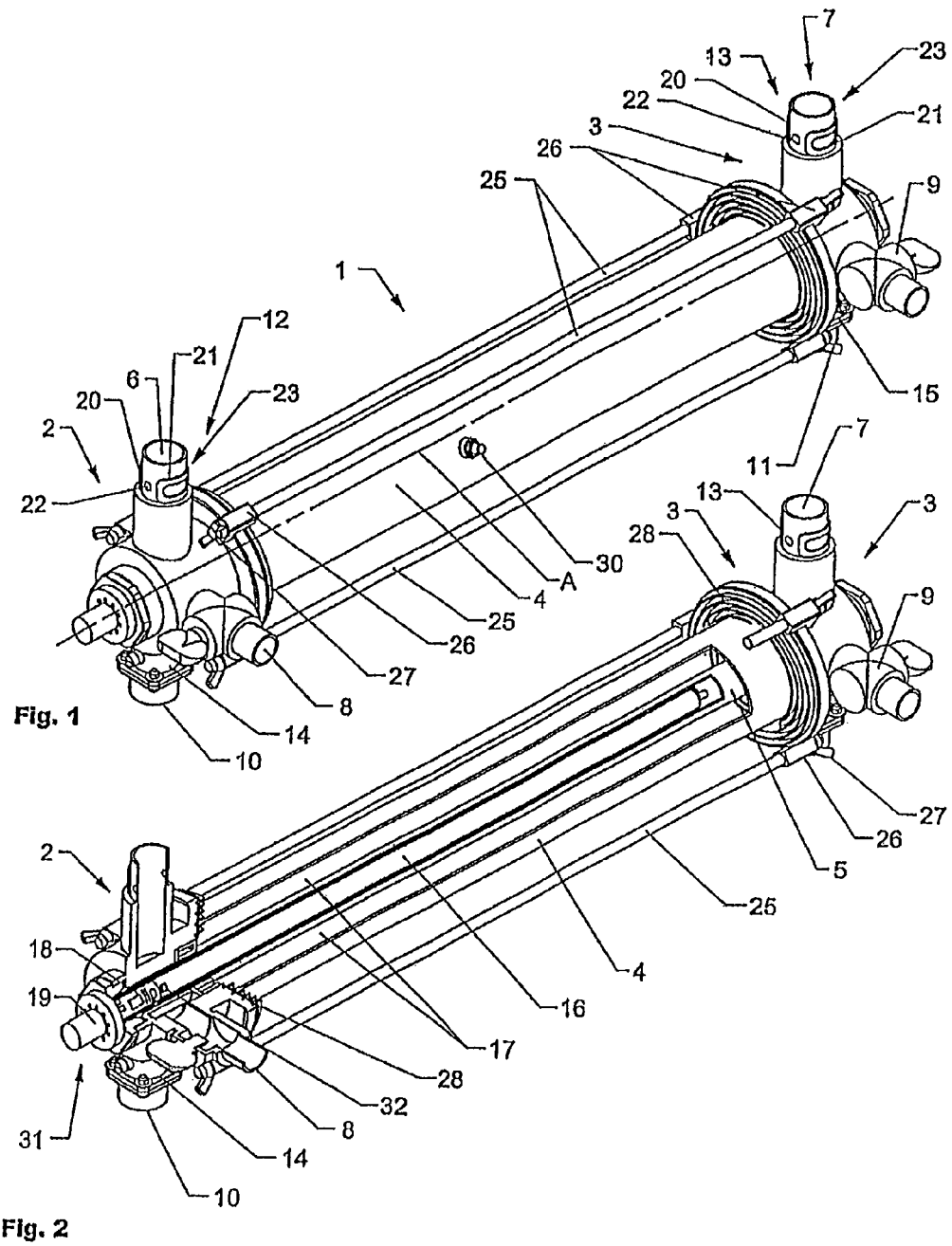

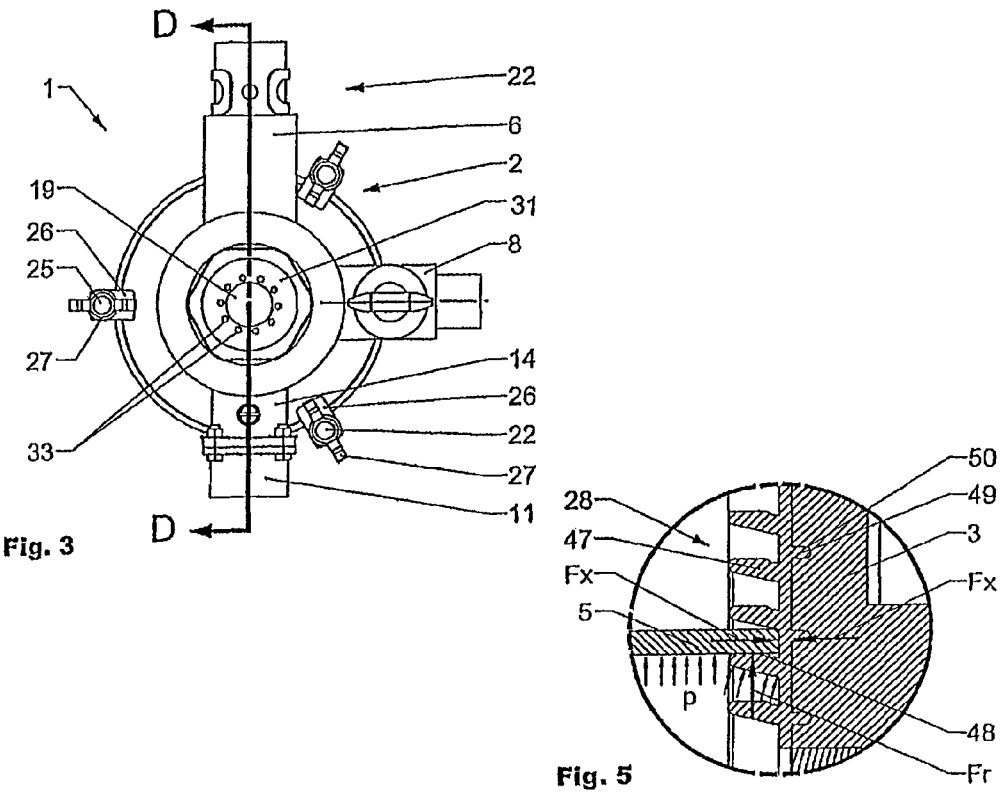
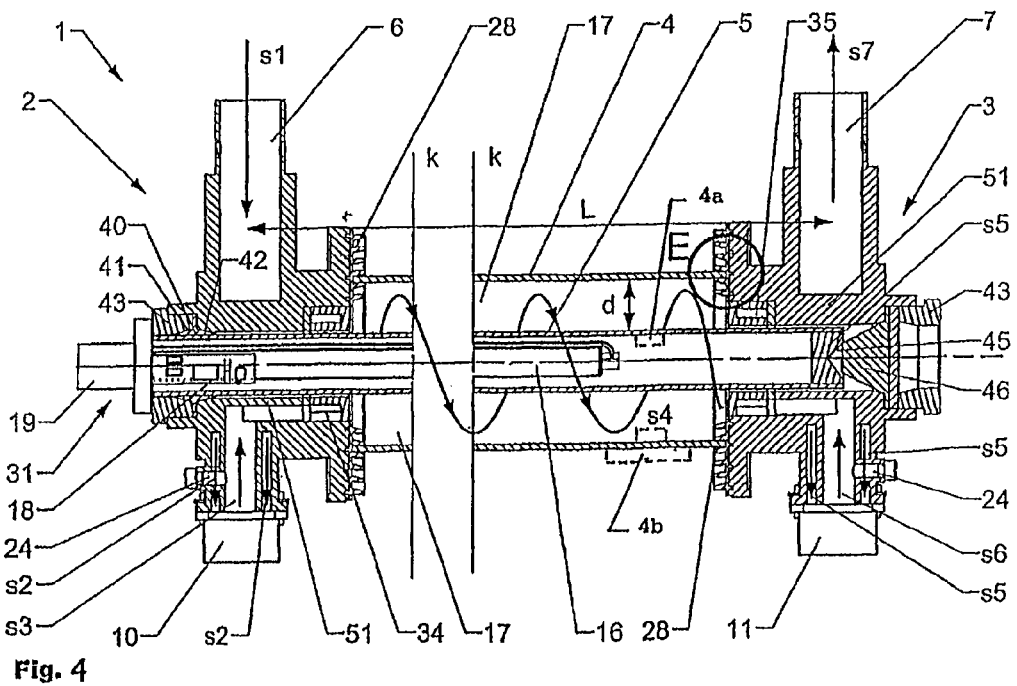

STERILIZING DEVICE AND A METHOD FOR STERILIZING OF FLUIDS

TECHNICAL FIELD

The invention concerns a sterilizing device for sterilizing of a fluid by UV-radiation comprising at least one UV-lamp for emitting UV-radiation, a lamp tag attached to or incorporated in the at least one UV-lamp comprising information regarding the UV-lamp.

The invention concerns also a sterilizing method for sterilizing of a fluid by UV-radiation comprising at least one UV-lamp for emitting UV-radiation, a lamp tag attached to or incorporated in the at least one UV-lamp comprising information regarding the UV-lamp.

BACKGROUND ART

From the prior art it is known that fluids such as water or air can be sterilized by ultraviolet (UV) radiation. The fluid to be sterilized is therefore exposed to a source of UV radiation for a specific time.

CH 477 825 shows a device for sterilizing a fluid by UV radiation. The fluid is exposed to UV radiation in a gap between an inner and an outer tube which are arranged concentrically to each other. In the gap between the inner and the outer tube turbulence generating elements are arranged to prevent laminar flow of the fluid. The tube in which the UV-lamp is arranged is closed on one end.

U.S. Pat. No. 6,402,926 shows a device for sterilizing a fluid with a removable UV lamp. The fluid to be treated is guided through a gap between an inner and outer tube wherein a spiral-shaped device is arranged in this gap preventing laminar flow of the fluid. The outer tube is straight or U-shaped and the inner tube, in which the UV-lamp is arranged, is made of UV-transparent material and is closed on one end.

WO 00/14018 is directed to a sterilizing device for a fluid. The sterilizing device comprises a first and a second sleeve which are arranged on opposite ends of an outer tube. In the outer tube an inner tube is arranged concentrically. The inner tube which forms the housing for the UV-lamp is made of UV-transparent material and is closed on one end. The sleeves and/or the tube are made out of plastic or aluminum.

U.S. Pat. No. 6,693,397 shows a lamp source device which emits illuminating light in an endoscope. The device unit comprises a housing that includes a CPU for measuring the illumination time of the light-source and an antenna for sending the illumination time measured by the CPU to the lamp unit. The lamp unit comprises a housing for a Xenon-Lamp. An RFID tag is fixed to the housing of the lamp. The RFID tag has an antenna for receiving the illumination time information sent from the antenna of the housing and a rewriteable memory for storing the illumination time information received by the antenna of the tag.

WO 00/78678 discloses a water treatment system comprising an inductively coupled ballast circuit, a first subunit in the form of a UV-lamp-unit and a second subunit in the form of a filter unit. The water treatment system is designed for end of pipe and table units, only for small amounts of water. The water does not The UV-lamp-unit is inductively coupled for non-contact power transfer. The radio frequency identification system includes an ultraviolet light transponder that is located in the ultraviolet lamp assembly. In addition, the radio frequency identification system includes a filter transponder that is located in the filter assembly. The ultraviolet light transponder and the filter transponder communicate, using radio frequency, with the radio frequency identification system. Each transponder contains certain information that is specific to the ultraviolet lamp assembly and the filter assembly. Alternatively a non-wireless identification system may be used instead of the radio frequency identification system.

WO 00/78678 is directed to an electronic control system for a water treatment system that includes an inductively coupled ballast circuit. The water treatment system filters water by, amongst other things, directing a flow of water from a water supply to a filter assembly. The filter assembly removes unwanted particulates from the flow of water. After passing through the filter assembly, the water is directed to a replaceable ultraviolet lamp assembly. The ultraviolet lamp assembly destroys organic matter in the supply of water by exposing the water to high-intensity ultraviolet light as the water flows through the ultraviolet lamp assembly. The overall operation of the water treatment system is controlled by a control unit that is electrically connected with the ultraviolet lamp assembly and the filter assembly. In the preferred embodiment, the control unit is also electrically connected with a flow sensor, an ambient temperature sensor circuit, an ambient light sensor circuit, an ultraviolet light sensor circuit, a power detection circuit, a display, an audio generation circuit, a memory storage device, a communications port and a radio frequency identification system. These devices are all monitored or controlled by the control unit.

The devices known from the prior art are using specific UV-lamps as available on the marked and are therefore in general committed to one type only. Due to the reason that common UV-lamps are subjected to aging, which results in a decreasing performance of the UV-lamps, they have to be replaced frequently to guarantee save sterilization of the fluid. To reduce the risk of insufficient disinfection of the fluid the UV-lamps are replaced after a certain period of time even though they have not yet achieved the end of their lifetime. In the case of failure of the source of radiation e.g. by contamination of the source of radiation, by oxidation of contacts or maltreatment, the devices known from the state of the art do not offer the opportunity to indicate such incident. Therefore these devices carry a relatively high burden of risk and are therefore very cost intensive due to frequent maintenance and early replacement of the source of radiation to guarantee save function. Higher reliability is tried to be achieved by more expensive UV-lamps resulting in the draw back of higher operating costs.

DISCLOSURE OF INVENTION

One problem to be solved by the herein disclosed invention is to provide an improved device for sterilizing a fluid offering the opportunity to actively control the device and/or the fluid and the degree of disinfection.

A further problem to be solved is the save substitution of expensive UV-lamps by the implementation of lower cost UV-lamps such that operating costs can be reduced without reduction of functionality or safety.

A further problem to be solved is to provide a device easily adoptable to different demands.

A still further problem to be solved is to provide a device which is not committed to a single type of UV-lamp.

The problems are solved by the sterilizing device of the present invention as defined by the preamble, characterized in that said lamp tag is interconnected with a lamp sensor unit and/or a control unit.

The sterilizing devices according to the present invention preferably comprise a modular setup which offers the opportunity to assemble specific devices depending on the field of application and flow rates. Compared to end of pipe devices, as known from the prior art, the modular sterilizing devices are, depending from their setup, capable to handle volume rates between 0.5 m3/h and 100 m3/h per unit.

A preferred sterilizing device according to the present invention comprises an inner tube, forming the housing for a UV-lamp, which is made out of a UV-transparent material such as quartz glass (vitreous silica) and an outer tube, arranged concentrically to the inner tube, which is preferably made of a UV-transparent material or out of a UV-reflecting material (e.g. aluminum). In a gap which is arranged between the inner and the outer tube the fluid to be treated is exposed to the UV-radiation of the UV-lamp arranged in the inner tube. The thickness of the gap is chosen depending on the fluid and the volume per time of fluid to be treated. The inner and the outer tube end at least on one side in a flange. Preferably at least one flange comprises a housing for one or more sensors and/or a control unit for a lamp and/or a sensor and/or other devices, such as ventilation for cooling/and or heating, if available.

A preferred embodiment of a device according to the present invention preferably has a modular set-up such that it can be easily assembled and disassembled. The flanges are preferably made out of plastic by injection molding. The plastic material may comprise glass or aramid fibers to increase the strength of the material. Alternative materials such as metal or ceramics may be used. The flanges preferably have a symmetric set up such they can be manufactured by a single mould. Compared to devices made of metal, one benefit of plastic material is the transparency for radio waves offering the opportunity to exchange information wireless.

The flanges in general comprise a main connecting piece serving as in- or as an outlet for the fluid to be treated. In the area of the main connecting piece a valve gate may be arranged which can be operated manually or which is interconnected to the control unit of the device, such that the disinfection process may be interrupted if necessary. Alternatively a filter device may be arranged instead of or in addition to at least one valve gate. The flange may comprise a standardized interface suitable to receive a valve gate and/or a filter device and/or another device or more may be connected in series or parallel. The devices may be interconnected by a suitable adapter unit. The standardized interface preferably has a coaxially shaped passage for the fluid to be treated. Alternative embodiments are possible.

If applicable at least one flange is equipped or interconnected with a flow measuring unit to measure the amount of fluid passing through the sterilizing device. A preferred flow measuring unit is based on Faraday's law of induction, operating by measuring the change in voltage that occurs in electrically conductive fluid as it passes through a magnetic field. This design approach eliminates moving parts and reduces the need for maintenance. This offers the advantage that particles in the fluid being measured, its viscosity, or the presence of pollutants in general do not impact measurement accuracy. Depending on the field of application alternative flow meters may be applied. The flow meters are preferably arranged before or after a flange.

The devices known from the state of the art are difficult to clean and therefore often have to be dismantled to gain access. To simplify maintenance of the device the flange may comprise a secondary connecting piece which in normal operation is not connected. The secondary connecting pieces are used for cleaning purposes by setting up a circulation between the secondary connecting pieces with cleaning fluid.

The inner surface of the outer tube is preferably made of or coated with a material having good reflection coefficient for UV-radiation. Good results are achieved with aluminum. Care has to be taken that data transmission is not interrupted.

In difference to the prior art, the herein disclosed device in general comprises a control unit which is interconnected with sensors and/or servos. The control unit preferably is arranged in a housing. If necessary one control unit can be used to control more than one sterilizing device. Depending on the field of application the interconnection between the several parts of a sterilizing device can be done by wires. Alternatively or in addition very good results are achieved by wireless transmission of data e.g. by ZigBee which is nowadays promoted by several companies such as Honeywell, Invensys, Mitsubishi, Motorola and Philips as standard for remote monitoring and control applications. The ZigBee protocol has been designed from the ground up to support very long life battery applications and is therefore suitable to be used in the sterilizing device according to the present invention. Alternative or in addition protocols such as WiMax (802.16) which is designed for wireless broadband access up to 50 kilometers and up to 70 Mbit/s, WiFi (802.11a, b and g), designed for wireless transmission over tens of meters in range, or Bluetooth (subset of the 802.15) having a range of up to 10 meters.

In a preferred embodiment at least several parts of a modular sterilizing device are preferably marked by or incorporating Radio Frequency Identification Tags (RFID-Tags). These tags are controlled by a control unit, e.g. preventing wrong assembly of the sterilizing unit, respectively indicating the correct control variable to be applied. E.g. in a sterilizing device several UV-lamps may be used having the same outer shape, but different physical behavior, not distinguishable from the outside. These lamps are preferably marked by a RFID-tag which is connected to or implemented in them such that the control unit can distinguish what lamp is inserted into the device and e.g. prevent insertion of a wrong lamp or a lamp which exceeds it's life time. The housing of the sterilizing device and the plating, if existing, preferably are made out of material which is transparent for radio frequency such that information may be exchanged wireless.

The RFID-tag may comprise further functionality such as random access memory (RAM) and/or means such as sensors measuring the working life of the lamp, the intensity of the radiation. Depending on the field of application this information may be stored in the RFID-tag or transmitted to the control unit. The RFID-tag of the lamp may be important to guarantee save function of the sterilizing device.

In a sterilizing device RFID-tags may be also incorporated in flanges, valves, control units, pumps or sensor units to indicate to a central unit whether the setup is correct or not. The RFID-tags may hold only a small amount of unique data, such as a serial number or other unique attribute of an item. The data can be read from a distance, therefore no contact or wire connection is necessary. In general an RFID-tag contains an antenna, and a small chip that stores or processes data. The RFID-tag can be programmed at manufacture or on installation and may be powered e.g. by a high power electromagnetic field generated by an antenna, such that the field allows the chip/antenna to reflect back a signal containing data. A collision detection, which allows recognition of multiple tags in the read range, is employed to separately read the individual tags. Active RFID-tags have an own power supply e.g. battery or solar cell. They have a greater range (up to 100 m) and may hold more data. Tags may be equipped with or connected to sensors e.g. to measure temperature, pressure, intensity of radiation, flow rate of fluid. A central unit may preferably be programmed according to the task to be solved.

E.g. the setup of a sterilizing device for drinking water is different compared to the setup of a sterilizing device for a swimming pool. These different setups may be programmed in the central unit such that correct assembly and functionality is guaranteed during the whole lifetime of the device.

Sensors are preferably arranged at different location within or outside a sterilizing device controlled by a control unit such that save operation is guaranteed. Several sensors are preferably arranged within the inner tube of the sterilizing device. E.g. a first sensor is arranged such that it measures the radiation emitted by the UV-lamp. A second sensor is arranged such that it measures the radiation reflected by the inner surface of the outer tube, e.g, indicating whether contamination or tramping of the surfaces is present and the device has to be cleaned. A third sensor is measuring the presence of a fluid in the gap between the inner and the outer tube, a fourth sensor is measuring the temperature of the fluid, a fifth sensor is measuring the temperature in the inner tube and of the lamp. These sensors preferably are incorporated in a sub device having it's own control unit and power supply (e.g. in the form of a foil battery). A sixth sensor may be arranged on the outer tube to measure UV-radiation. The sub device is preferably interconnected to a main control unit by wire or wireless. The above mentioned sensors, the control unit and the power supply preferably are arranged on a platform which is formed such that it can be clamped in between the UV-lamp and the inner tube.

In addition or alternative to a control unit, the sterilizing device may comprise a lamp- and media-monitoring unit which e.g. may be clamped at a UV-lamp or between the inner tube and the UV-lamp. In a preferred embodiment the lamp- and media-monitoring unit comprises a base with several sensors. A thermo element is used to measure the temperature at the surface of the UV-lamp. A first photo element records the intensity of the radiation emitted by the UV-lamp and a second photo element records the intensity of the radiation of the UV-lamp reflected by the inner surface of the outer tube, which did pass any sedimentation and contamination of the device. By this it is possible to determine whether it is necessary to clean the device. A media sensor, preferably capacitive, is used to determine whether the fluid to be treated is a gas or a liquid. To supply the electronic circuit with electrical power, the lamp- and media-monitoring unit is equipped with a power source, e.g. a foil battery or a photo element. The photo element is preferably arranged on the inner surface of the base, which is exposed directly to the radiation of the UV-lamp, such that the emitted radiation of the UV-lamp is used to drive the photo element. Depending on the field of application the lamp- and media-monitoring unit may be supplied by external energy. A suitable microprocessor controls the sensors. The microprocessor is interconnected with an antenna to exchange information with a main control unit wireless. Alternatively or in addition the microprocessor communicates by wire with the outside. In a specific embodiment the temperature of the UV-lamp and/or the media can be controlled by an infrared sensor.

Accepting the related drawbacks and depending on the field of application the herein described embodiments of hardware of a sterilizing device may be, if appropriate, equipped with conventional UV-lamps and drive units without sensors and control units.

Depending on the setup of the device, the inner tube may extend from one flange to the other being open on both ends offering the opportunity for straight-through ventilation of the inner tube. Alternatively the inner tube may be sealed at least on one side.

The herein described sterilizing device may incorporate a filter and/or an ultrasonic device interconnected to one of the flanges or between one of the flanges and the outer tube. The filter preferably is developed as a modular unit which can be e.g. clamped between one of the flanges and the outer tube.

A preferred embodiment of the invention comprises a sterilizing device having a modular setup. The several modules are interconnected to each other by standardized interfaces offering the opportunity that several alternative modules may be interconnected depending on the field of application, type and volume (e.g. due to several sources with different cloudiness) of fluid to be treated. Thereby it becomes possible to assemble, based on a given set of modules, a sterilizing device e.g. for drinking water, treatment of a swimming pool or special treatment of fluids in chemical industry. Typical modules are alternative inner and outer tubes, having different diameters; different flanges; different sensor units, such as pressure, temperature and UV-sensors or any disinfection device e.g. electrochemical, oxidant fluids; filter units; pumps. The sterilizing device is equipped in general with at least one valve gate. However, certain applications such as for a swimming pool do not request a valve gate. This offers the advantage that sterilizing devices may be distributed as a kit of parts to be assembled specifically according to the field application.

Each of the modules may be marked by an identification tag which provides a control unit with information about the module itself an it's capabilities, e.g. such as dimensions, pressure and flow rates and type of use. The control unit may be factory programmed or programmed while assembly of the device such that optimal performance and security is given. E.g. if a sterilizing device is assembled in a wrong way or if a part is missing, the control unit prevents a valve gate to open, such that no fluid may enter the sterilizing device. A control unit is preferably interconnected with sensors and servo units, such as valve gates and/or bulkhead units to control the amount of UV-radiation emitted by the UV-lamp. The identification tags or additional tags may comprise or may be interconnected to a logic circuit, a memory and/or a sensor for collecting and exchanging information with the at least one control unit. The modules preferably exchange information wireless, e.g. based on radio frequency. RFID-tags may be developed as subunits solving there own dedicated task.

A sterilizing device may be interconnected with a motion sensor triggering the ignition of the UV-lamp. This setup offers the opportunity to save energy e.g. during night time or in installations with irregular time schedule such as holiday homes.

A sterilizing device according to the present invention may be equipped additionally with a further device based on pulsed-power to eliminate mineral scale and/or control microbiological populations and/or control corrosion. It has been shown that by inducing a time-varying magnetic field a rapidly changing electric field in a fluid system of the same frequency as the magnetic field but in a direction around the circumference of the pipe may be generated. The coil for such a procedure is preferably wound around the inner and/or the outer tube of the sterilizing device. By inducing the field it is possible to shift the equilibrium chemistry of Calcium carbonate to favor formation of stable crystal nuclei in the bulk solution. Thus crystal growth and precipitation can be controlled such that it can be filtered as a loose powder instead as a scale on a surface. Alternatively or in addition the further device may be interconnected over an interface flange.

The problems are also solved by the method according the preamble of the invention, characterized in that said the fluid to be treated is submitted at least to the following treatment phases:
- a step of mechanical filtering
- a step of fluid quality monitoring online analysing and determination
- a step of dosing of fluid oxidant
- a step of UV-radiation when it flows trough a space defined between an inner and an outer tube.

The step of dosing of fluid oxidant is preferrably combined with the UV-radiation to increase the sterilization effect of the UV waves.

According to a preferred option, the fluid to be treated may furthermore be submitted to power ultrasonic waves for providing a cavitation effect in the fluid for destroying contaminants like bacteria and/or various microbes and/or plancton.

According to another option, the fluid to be treated may furthermore be submitted to a step of dosing of the treated fluid for reaching lasting effects, mineralization and aromatization.

BRIEF DESCRIPTION OF DRAWINGS

Several embodiments of the invention are described in detail according to the following figures:
FIG. 1 shows a first embodiment of a sterilizing device in a perspective view;
FIG. 2 shows the first device according to FIG. 1 partially cut;
FIG. 3 shows the first device according to FIG. 1 in a side-view;
FIG. 4 shows a cross-cut through the first device according to FIG. 3 along line DD;
FIG. 5 shows a detail E of a sealing of FIG. 4.

MODE(S) FOR CARRYING OUT THE INVENTION

Figure 6:
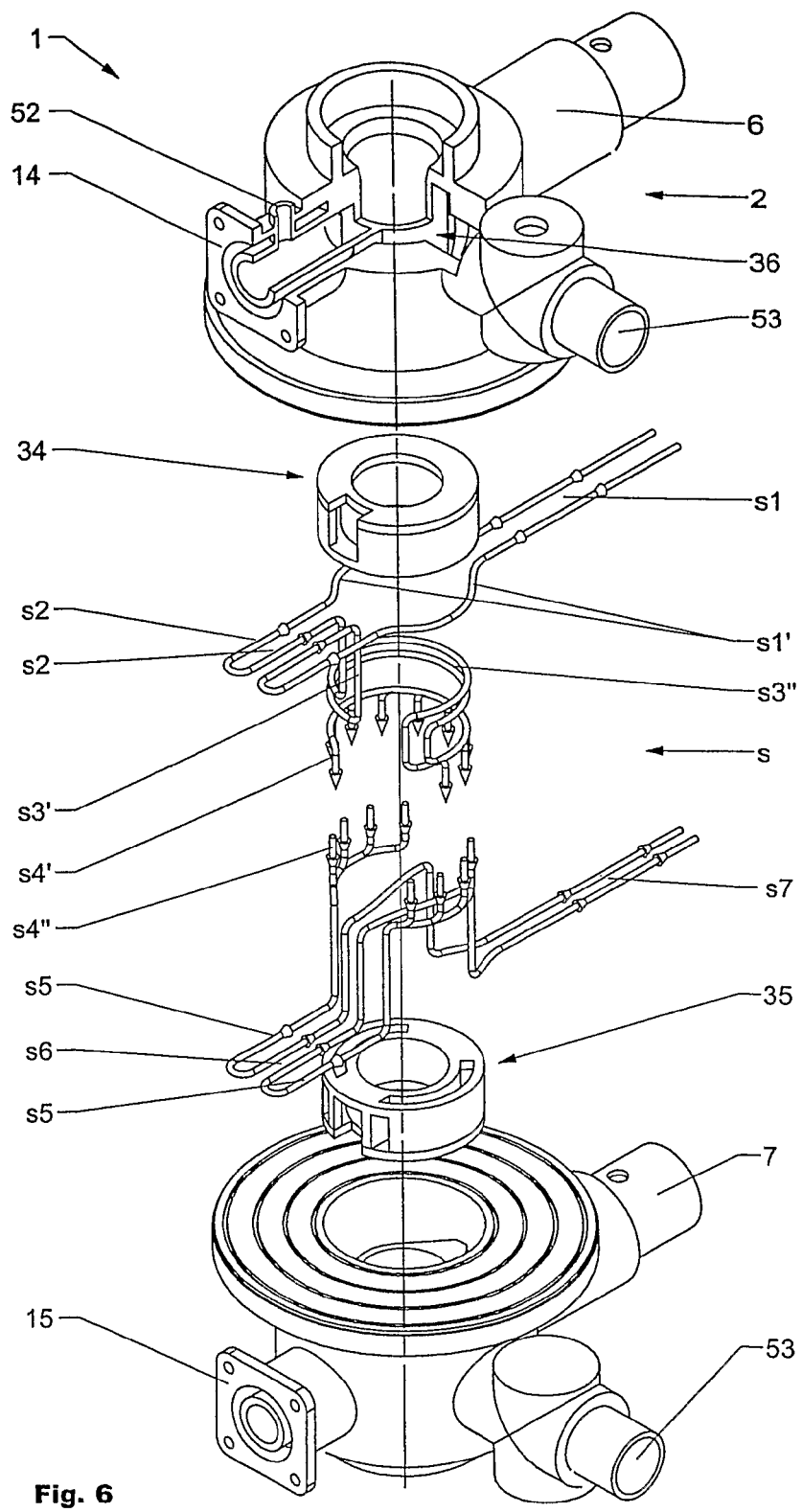
FIG. 6 shows a flow path through a sterilizing device.

FIG. 1 and FIG. 2 show a first preferred embodiment of a sterilizing device 1 respectively in a perspective view and in a partially cut view offering the possibility to look at the inside. The shown embodiment comprises a first and a second flange 2, 3 arranged on opposite ends of an inner and an outer tube 4, 5. The first and the second flange 2, 3 each are comprising a main connection piece 6, 7, a secondary connection piece 8, 9, a valve gate 10, 11 and a flow measuring device 12, 13. The base module of the first and the second flange 2, 3 are in this embodiment similar to each other and are made, here made out of injection molded plastic. To increase abrasion resistance the surfaces may be at least partially coated by or comprise ceramic or metal inserts. To improve mechanical strength the elements made out of plastic may comprise fibers e.g. such as glass-, Kevlar or carbon. Alternatively or in addition the elements are made at least partially out of metal, such as aluminum or steal. The flanges 2, 3 are each comprising an interface flange 14, 15 suitable to receive a standard valve gate 10, 11 and/or a filter unit and/or a pump and/or control units, such as a water counter. The interface flanges 14, 15 are serving as standardized interfaces to connect, if necessary, further modular units to the sterilizing device 1 such that the setup is adoptable to different requests. The functionality may be enhanced by interfaces as shown in detail in FIG. 13.

The sterilizing device preferably comprises at least one valve gate downstream to control defects. Due to this setup it is possible to provide highly integrated devices. The valve gates 10, 11 of the present embodiment are of a standard type and may be opened and closed remotely by a signal of a control unit or control switch. By opening an closing the first and the second valve gate it is possible to control the flow of the fluid which passes through the sterilizing unit 1. E.g. in the case of urgency or for maintenance reason the flow may be stopped completely by closing the valve gates 10, 11 automatically or manually. The valve gates 10, 11 are arranged in the herein shown embodiment between the first and the second flow measuring devices 12, 13. Depending on the field of application at least one valve gate may be arranged alternatively or in addition on the opposite side of at least one flow measuring device 12, 13. The valve gates may be used to treat a fluid in sections e.g. in the case of highly contaminated fluid.

In this embodiment each of the flanges 2, 3 comprises at least a flow measuring device 12, 13 to determine and/or count the amount of fluid passing through the sterilizing device. The flow measuring devices should be robust, low cost and applicable for turbulent or laminar flow. Good results may be obtained by magnetic, inductive or capacitive flow measuring devices. It is preferable that the flow measuring devices are not position sensitive, e.g. by having negative impact on the range of application of the sterilizing device 1. In electrically conductive fluids, such as certain liquids, good results may be achieved by inductive flow measuring devices which are based on Faraday's law of inductivity. The flow measuring device comprises a first and a second coil 20, 21 to generate a magnetic field in between. The coils 20, 21 are arranged such that the fluid to measured passes through magnetic field. By two electrodes 22, 23, arranged opposite to each other and in contact with the fluid to be measured, a resulting voltage may be measured which is proportional to average flow velocity. The electrodes 22, 23 may not be arranged in electrical contact to each other by the housing of the flange 2, 3.

The flow measuring device are preferably incorporated in the flanges in the area of the main connection pieces 6, 7, e.g. by incorporating in the molding process of the flanges or as a separate part which is mounted at a later stage and glued, welded, clamped or ultrasonic welded to the flanges 2, 3. By incorporating the coils 20, 21 and the electrodes 22, 23 in the flanges the production costs and the efforts regarding assembly of the device may be reduced. The flow measuring devices 12, 13 are serving as a sensor, important to control the performance and reliability of the sterilizing device 1. The sensor output may be used to adjust the capacity of a ultra violet source, in the present embodiment in the form of a fluorescent lamp 16 which is arranged in the inner tube 5. By taking the mean of the first and the second flow measuring devices 12, 13 the accuracy of measurement may be increased.

In this preferred embodiment, the device comprises additionally a water quality monitoring, an analysing and determination sensor (not represented in the drawings) which may be mounted (see 8 or 9) or integrated nearby the first and second flow measuring device 12 and 13 or on the fluid entrance main connection piece 6 or 7 or integrated somewhere in the fluid entrance flange 2 or 3. This fluid quality monitoring sensor is preferably a membrane less sensor type as for example the device commercialized under the trademark AuSenSys™ of the Swiss company ADAMANT AG. The said fluid quality monitoring sensor is adapted for online measuring dissolved oxygen, disinfectants/oxidants such as chlorine, peroxodisulfate, $O_3$, $H_2O_2$, and heavy metals, like CrVI, Cd. Pb, Ag, Cu.

The inner tube 5 is preferably made out of a material which is transparent for UV-radiation emitted from the UV-lamp 16 such that fluid which flows through a gap 17 between the coaxially arranged inner and outer tube 4, 5 is exposed to and treated by the UV-radiation. In the gap 17 additional vortex generating means may be arranged to prevent laminar flow of the fluid. The inner tube 5 is preferably made out of quartz glass (vitreous silica) and the outer tube 4 out of a UV-reflecting material (e.g. aluminum).

The output of at least one flow measuring device may be used to measure or determine the amount of water (water counter) consumed in a water distributing system, e.g. such as a household or stand alone water kiosks in an area where water is rationed. An electronical device such as an RFID tag may be provided to store and/or transmit data to a stationary or a temporary passing by remote device. This offers the opportunity that e.g. a water meter may be read independent of the presence of the tenant of a house.

In certain embodiments the voltage produced by the flow measuring device may be used to drive an electronic circuit e.g. an RFID tag which offers the opportunity to transmit the measured data wireless or by wire to a control unit.

The coils 20, 21 and/or the electronic circuit may be driven by an integrated battery (e.g. a foil battery) which lasts sufficiently long and may be exchanged while routine maintenance. In addition or as an alternative to the external driven coils 21, 22, permanent magnets (not shown in detail) may be used to produce the magnetic field necessary to measure velocity. The flow measuring devices 12, 13 may be coupled directly or indirectly to the valve gates (proportional or on-/off-type) to adjust the amount or the velocity of the fluid to be treated.

Each of the flanges 2, 3 of the herein described embodiment comprises a secondary connection piece 8, 9 which may be opened an closed manually. The secondary connection pieces are serving e.g. as bypasses, for maintenance of the device or if untreated or treated liquid has to be taken from the system or for interconnecting further devices such as electrodes, etc. Depending on the field of application the secondary connection pieces 8, 9 may be avoided.

The flanges 2, 3 and/or the tubes 4, 5 may incorporate a pressure sensor to measure the pressure of the fluid to be treated. The outer tube 4 is clamped in between the first and the second flange 2, 3 by three tie rods 25 which are connected to the flanges 2, 3 on each side by clamps 26 and clamping screws 27. Due to the reason that the internal pressure is acting on the flanges 2, 3 a sensor to measure the pressure in the sterilizing device 1 may be incorporated in or installed closed to at least one tie rod (e.g. by a tag measuring the tension of a tie rod). The sterilizing device 1 is constructed such that the first flange 2 can be fixed with reference to the second flange 3 in almost any angular position with respect to the central axis A, such that the device offers a wide field of applicability. The main connection pieces 6, 7 may be arranged at any angle between 0° and 360° to each other.

Between the flanges 2, 3 and the outer tube 4 a first gasket 28 is arranged. The first gasket 28 of the shown embodiment is suitable to fit, e.g. by replacement, different diameters of outer tubes 4 such that the sterilizing device can be adjusted according to the field of application, velocity, volume and pressure of the fluid to be treated. The first gasket 28 and its functionality will be described in more detail in accordance with FIGS. 4 and 5.

In this embodiment, on the outer surface of the outer tube 4 a sensor device 30 is visible which extends through a bore in the outer tube 4 into the gap 17. The setup of the sensor device 30 is preferably modular such that it can be adopted according to the task to be solved. Depending on the field of application the sensor device 30 is used to measure the intensity of radiation emitted by the UV-source 16. By this arrangement of the sensor device 30 it is possible to gain information about the transparency of the fluid to be treated in the gap 17 and/or the inner tube 5. Therefore it is possible to control whether the fluid to be treated is to cloudy or whether the sterilizing device needs maintenance due to contamination. Alternatively or in addition the sensor device 30 may be used to measure the temperature and/or the presence and/or the velocity of the fluid to be treated. The sensor device 30 is preferably interconnected with a central unit. If applicable the sensor unit 30 may be an RFID tag. The RFID tag may be driven by the radiation of the UV-lamp (e.g. by a photo sensor).

The sterilizing device of FIG. 2 is partially cut such that it is possible to look at the inside of the sterilizing device 1. Through an opening in the first flange 2 a lamp unit 31 extends into the inner tube 5, comprising the UV-lamp 16, a lamp sensor unit 18 and a bulkhead/control unit 19 which serves to control the UV-lamp 16. The UV-lamp 16 is equipped with a lamp tag 32 which comprises information about the lamp 16. The lamp tag 32 communicates with a control unit (not shown in detail) and/or the lamp sensor unit 18 and/or the bulkhead/control unit 19 preferably wireless by radio frequency. The lamp tag 32 may comprise a UV-sensor, a logic circuit and a memory, such that the tag may be suitable for measuring the amount and the intensity of UV-radiation emitted by the UV-lamp 16. Information e.g. about the intentional aging, the total operating lifetime and the switch-on/off cycles of the lamp 16. The lamp tag 32 may be designed as a stand alone unit which can be used independently of an additional control unit suitable to control installations having a large amount of fluorescent lamps. The data from the lamp tag unit 32 may be retrieved from remote continuously or only at specific times. The lamp tag unit 32 preferably is attached to the glass cylinder or any other suitable position of the lamp 16 in a way that the lamp unit tag 32 may not be removed from lamp without destruction. The lamp tag unit 32 may comprise a detecting agent (e.g. an LED-display) to indicate information about the lamp 16. On specific fields of application the lamp tag 32 may be incorporated in the lamp sensor 18.

Accepting the related drawbacks the herein described hardware may be equipped instead of lamp sensor and bulkhead units 18, 19 with standard UV-lamps and drive units even though control and reliability of the sterilizing process may suffer.

FIG. 3 shows a side-view of the device according to FIGS. 1 and 2. The lamp unit 31 which is arranged coaxially to the inner and the outer tubes (not visible here) extends through the first flange 6 into the inner tube (not visible here). Next to the control unit 19, which is in this embodiment incorporated in the lamp unit 31, ventilation openings 33 are visible which serve for ventilation of the lamp and the inner tube (not visible here). The tie rods 25, the clamps 26 and the clamping screws 27 serve to securely close the sterilizing device 1. The sterilizing device preferably has a setup which can be assembled and disassembled without special tools. Permanent welding connections are in general avoided when they are contradictory to the modular design. A cross cut along line DD is displayed in FIG. 4.

FIG. 4 shows the cross cut through the sterilizing device 1 according to FIGS. 1 to 3 along line DD. The sterilizing device 1 is displayed in a reduced length which is indicated by the lines kk. The flow path of a fluid through the sterilizing device 1 is indicated schematically by arrows s1, s2, s3, s4, s5, s6, s7. Detailed explanation of the flow path of the fluid is given in accordance with FIG. 6.

When the valve gates 10, 11 are open the fluid enters the sterilizing device through the first main connection piece 6, indicated by arrow s1, is then piped on both sides around a centrally arranged tube housing 51 which extends continuously through the flange 2 and comprises the inner tube 5 and, as indicated by arrows s2 and s3, passes then through the first valve gate 10 arranged opposite to the first main connection piece 6 on the back of the first flange 2. After then the fluid is guided through a, in this embodiment exchangeable, vortex unit 34 into the gap 17 between the inner and the outer tube 4, 5 where the fluid is exposed to the UV-radiation emitted by the lamp 16. The vortex unit is arranged around the inner tube 5 and deflects the flow of the fluid on a path, schematically indicated by arrows s4, on a helix like path around the inner tube 5. Depending on the field of application the vortex unit 34 may be developed different such that other flow paths, e.g. such as highly turbulent or laminar flow is achieved. In the gap 17 additional or alternative vortex elements (not shown in detail) may be arranged. Before entering into the second flange 3, the fluid passes through a in this embodiment exchangeable conveyer unit 35 which guides the fluid onto a different path through the second valve gate 11, indicated by arrows s5 and s6, and then, as indicated by arrow s7, through the second main connection piece 7 out into an adjacent pipe system (not displayed in detail).

In one embodiment the flanges 2 and 3 comprise a mechanical treatment system 36 wherein decomposition of organic and chemical contamination is achieved by high shear forces and/or negative pressure. Preferably this mechanical treatment system 36, the so-called flow former, may be integrated in the flanges 2 and 3. Due to the design of the flanges 2, 3 the fluid is accelerated to high velocity of flow (typically in the range of 100 m/s to 300 m/s), e.g. by vents. By guiding several vent streams into each other high shear forces result. In connection with centrifugal forces this leads to a mechanical cracking of organic contamination. In an area with negative pressure germs are destroyed due to low pressure.

In a preferred embodiment an additional ultrasonic reactor may be provided for destroying contaminants such as bacteria for example. Such a reactor 4a, 4b is schematically represented in FIG. 4. The reactor 4a is located outside of the outer tube 4, attached to the outer surface of the tube or as a cylindrical unit between the flanges 2,3 inline with the outer tube 4 (not represented in the drawings). The reactor 4b is located inside of the outer tube 4, attached to the inner surface of the tube or to any support mounted inside of the outer tube 4 or a needle reactor integrated in the heel 46 (not represented in the drawings). The reactor 4b may have the shape of a ring, a cylinder or a cone or any other adequate shape adapted to transmit power ultrasonic waves to the fluid to be treated. The reactor 4b, is directly in contact with the fluid to be treated. The reactor 4a is in direct contact with the outer tube which transmits the ultrasonic vibration first to the outer tube and than to the fluid to be treated. Contaminants like bacteria for example are destroyed by a cavitation effect induced by the ultrasonic power waves.

In the herein described embodiment of the sterilizing device 1 the inner tube 5 extends through the first flange 2 and is open on one side such that it can receive the lamp unit 31, comprising the lamp 16 and the lamp sensor 18. A second gasket 40 preferably made of a relatively deformable material e.g. such as rubber is arranged between a first and a second sealing surface 41, 42 of the first flange 2 and a coupling nut 43, which is screwed in the first flange, and adjacent to the inner tube 5. The first and the second sealing surface 41, 42 have a conical shape such that by tightening of the coupling nut 43 the second gasket 40 is pressed against the first and the second sealing surface 41, 42 and the inner tube 5 such that a pressure tight connection results and the inner tube is clamped in position. The shown embodiment offers the advantage that it is suitable to receive inner tubes with different diameters. In general only the second gasket 40 needs to be exchanged to receive a inner tube 5 having a different diameter. Alternatively the sealing surfaces 41, 42 may be part of exchangeable inlay parts (not shown in detail), which are arranged between the flange 2 and the coupling nut 43, and being adapted to the diameter of different inner tubes 5.

As it can be seen, the inner tube 5 is on the opposite end tightly closed by a plug 44 preventing fluid to enter into the inner tube 5. The plug 44 does have a recess 45 which rests in normal position on a heel 46 attached to the second flange 3. The inner tube 5 of the described embodiment does not continuously extend into the second flange 3 and can therefore, e.g. for maintenance reason, after loosening the coupling nut 43 and removing the second gasket 40 pulled out through the first flange 2. The heel 46 is preferably made of a rubber like material which decelerates the tube 5 when reentered into the sterilizing device 1 preventing damage. The heel 46 is arranged instead of a second gasket and is fixed by a coupling nut 43.

The first gasket 28 is arranged between the outer tube 4 and the flanges 2, 3. The gasket 28 is capable to correspond with outer tubes 4 having different diameters, such that is possible to adopt the sterilizing device 1 to different fields of application, flow rates and flow speeds. However even though more parts are necessary it is alternatively possible to use a separate gasket for different outer tubes 4. The gasket is explained in more detail in accordance with FIG. 6 which shows detail E.

The length L of the inner, respectively the outer tube 4, 5 and the diameter d of the gap 17 between are relevant for velocity and the time the fluid to be treated is exposed to the UV-radiation of the lamp 16. By modifying these parameters, influence may be taken on the process.

FIG. 5 shows detail E of FIG. 4. The first gasket 28 is clamped between the outer tube 4 and one of the flanges 2, 3. The clamping force indicated by arrows Fx in axial direction derives from the tie rods 25 (see FIG. 1). The axial force Fx results in a face side sealing force. The first gasket 28 comprises several axially protruding concentric barriers 47 which are corresponding to different diameters of outer tubes 5. The barriers 47 are developed such that on one side they are right for centering the outer tubes 5 and second they are preferably built out such that they act as radial sealing due to internal pressure p. The barriers are made such that they are flexible, collecting and concentrating the internal pressure p such that there outer contact surface 48 is pressed by a radial force Fr outward against the outer tube 5 which is proportional to the internal pressure p. The sealing offers the advantages that the sealing force is proportional to the internal pressure p and that the first gasket 28 has a certain tolerance with respect to axial and radial imperfection and there fore is still pressure tight. The first gasket is centered with respect to the flanges 2, 3 by protruding centering elements 49 which mate with corresponding centering recesses 50 of the flanges 2, 3.

FIG. 6 shows schematically a typical flow path s through a first embodiment of a sterilizing device 1 according to the present invention. The sterilizing device 1 is not shown in full detail to avoid masking of the flow path s. The first and the second flange 2, 3, the vortex unit 34 and the conveyer unit 35 are shown in a disassembled way, due to the reason that they are important for the guidance of the flow path s. Corresponding sections of the flow path s are drawn on top of each other. A front section of the first flange 2 is cut away offering a view on the inside of the first flange 2 and the first interface flange 14.

The sterilizing device is normally connected to adjacent pipes or other units such as pumps or filters. These units are not shown in detail in the present drawing. When the valve gate units mounted on the first and the second interface flange 14, 15 are open the fluid enters the first flange 2 through the first main connection piece 6 and if fitted a flow measuring device (not shown in detail), indicated by section s1 of the flow path s. It is then separated and guided on both sides around the tube housing 51 which is indicated by section s1'. A mechanical treatment stage wherein decomposition of organic and chemical contamination is achieved by high shear forces and low pressure. On the back of the lamp housing 51 the fluid streams are then in a first sterilizing step directed against each other through suitable vents such that high shear forces and if appropriate a pressure reduction result acting as a first step of purification.

The fluid is then guided through the first valve gate 10, indicated by arrows s2 and s3, down into the vortex unit 34 (arrow s3'). Due to the shape of the vortex unit 34 the fluid is, as indicated by section s3", deflected on a spiral path and then guided jet-like into the gap between the inner and the outer tube of the sterilizing device 1, where the fluid is treated by exposure to the UV-radiation. Due to the vortex unit 34 the moment of impulse of the fluid has increased and the fluid spins on it's way to the second flange 3 around the inner tube (schematically indicated by section s4'). After passing through the gap between the inner and the outer tube the fluid is collected by the conveyer unit 35 (indicated by section s4") and guided into the second flange 3. The flanges 2, 3 are designed such that the flow path can be altered by the design of the vortex unit 34 and the conveyer unit 35. This offers the opportunity that only one flange design is necessary. In the second flange 3 the treated fluid is guided through the second valve gate unit (indicated by arrows s5 and s6) and then through the second main connection piece 7 (indicated by section s7). In the second main connection piece 7 the fluid passes, if equipped, another flow measuring device where the velocity and the volume may be determined.

In the present embodiment each of the flanges is equipped with maintenance openings which may be connected to each other by a pipe and an external pump (not shown in detail) offering the opportunity to clean the sterilizing device by an appropriate detergent. Therefore, compared to the prior art, it is not necessary to fully disassemble the sterilizing device. Alternative flow paths are possible.

Figure 7:
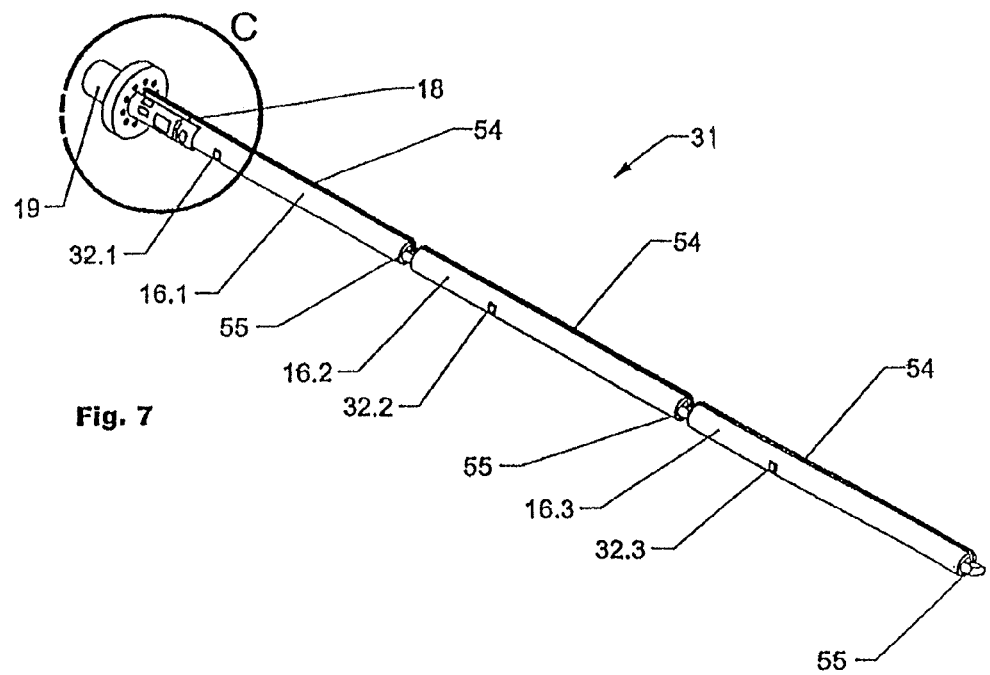
FIG. 7 shows a UV-lamp with a tag, a control unit and a sensor.

FIG. 7 shows a lamp unit 31 comprising a control unit 19 a lamp sensor unit 18 and three UV-lamps 16.1, 16.2, 16.3 of the same or different type/length are arranged coaxially to each other. Depending on the control unit 19 the lamps 16.1, 16.2, 16.3 of the same or different type/length are arranged coaxially to each other. Depending on the control unit 19 the lamps 16.1, 16.2, 16.3 may be activated independent and/or in pairs. The lap unit 31 is normally arranged in an inner tube of a sterilizing device or another suitable housing, e.g. a rack like arrangement. The UV-lamps 16.1, 26.2, 16.3 each are equipped with a lamp tag 32.1, 32.2, 32.3. The lamp tag 32.1, 32.2, 32.3 in general is equipped with a logical circuit, a memory device and a sensor device (not shown in detail). The lamp tags are interconnected, preferably wireless by radio frequency or by wire with the lamp sensor unit 18. The lamps 16.1, 26.2, 16.3 are connected to the bulkhead unit/control unit 19 by wires 54 and plugs 55. The lamp sensor unit 18 and/or the bulkhead unite 19 are interconnected to a main control unit (not shown in detail) by wire or wireless, depending on the field of application and the material of the housing. The lamp tags 32.1, 32.2, 32.3 comprise a UV-sensor, a logic circuit and a memory, such that the tag is suitable for measuring the amount and the intensity of UV-radiation emitted by the corresponding UV-lamp 16.1, 16.2, 16.3. The sensor is suitable to control information about the total operating lifetime, the intensity of the radiation and the switch-on/of cycles of the lamps 16.1, 16.2, 16.3. If applicable the lamp tags 32.1, 32.2, 32.3 may be arranged inside the lamps 16.1, 16.2, 16.3 in a way that the lap tags may not be removed from the lamp without destruction.

The present embodiment of the lamp unit 31 is suitable to be used in a sterilizing for varying fluid flow, e.g. in a house with several flats. At nighttime, when only a small amount of water is used, e.g. for rinsing a toilet or for a cup of drinking water only one lamp 16.1 is illuminated continuously sterilizing the amount of water needed at lower power consumption. In the morning, when the inhabitants are getting and more water is needed for making breakfast and showering a second and a third lamp 16.2, 16.3 may be lit guaranteeing that save disinfection of the water at higher flow rates. If applicable the lamp unit 31 may be equipped with a logical circuit which adopts automatically the power-up and the shutdown cycles to the habits of the system due to practical value.

Figure 8:
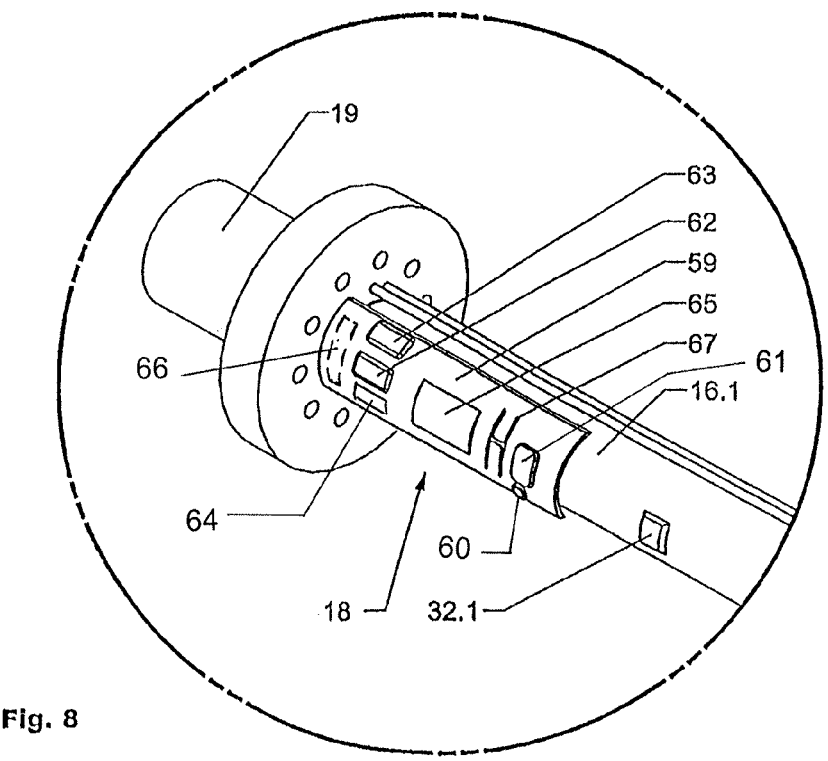
FIG. 8 shows detail D according to FIG. 7.

FIG. 8 shows schematically an enlarged view of the lamp sensor and control unit 18 and several of it's components according to detail C of FIG. 7. The elements of the control unit 18 are arranged on a curved base plate 59 which normally is arranged in a gap between a lamp 16.1 and the inner tube 5 (see FIG. 2). A preferred setup of the control unit 18 comprises the following components. A first UV-sensor 60 is arranged such that it measures directly the radiation emitted by the UV-lamp. A second UV-sensor 61 is arranged such that it measures the radiation reflected by the inner surface of the outer tube (see FIG. 1), e.g. indicating whether contamination or tramping of the inner tube and/or the outer tube is present. A third preferably capacitive sensor 62 is measuring the presence of a fluid in the gap between the inner and the outer tube. A fourth sensor 63, preferably based on infrared technology, is measuring the temperature of the fluid in the gap. A fifth sensor 64 is measuring the temperature in the inner tube and of the lamp avoiding extensional heat and to guarantee best sterilizing performance. The control unit 18 further comprises a controller 65 unit and power supply 66 in the form of a foil battery (arranged on the back of the base plate 59 and represented by dashed lines in the figure). The controller 65 is interconnected with the sensors and communicates with a main control unit (not displayed in detail) wireless by an antenna 67.

Figure 9:
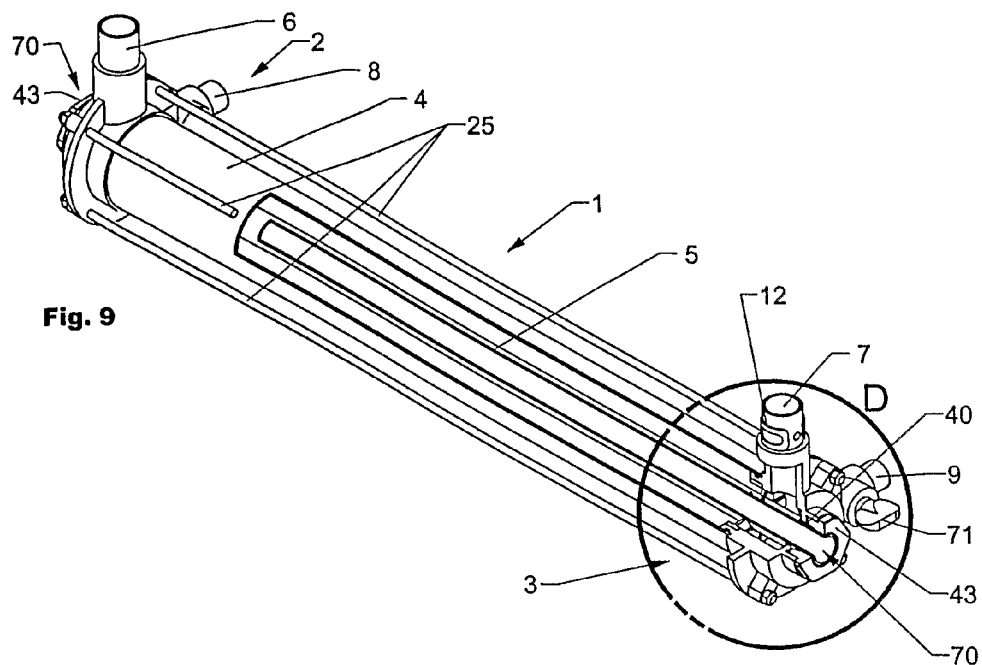
FIG. 9 shows a second embodiment of a sterilizing device in a perspective view.

FIG. 9 is showing a second embodiment of the sterilizing device 1 in a perspective view. A part of the device is cut away such that it is possible to view the inside. Between the first and the second flange 2, 3 the outer tube 4 is arranged. Four tie rods 25 are connecting the first and the second flange 2, 3 clamping the outer tube 4 in between. The first and the second flange of the present embodiment are having a symmetrical setup with central opening 70 wherein the inner tube 5, which is made of a UV-transparent material, is clamped by a coupling nut 43 and a second gasket 40 on each side. The inner tube 5 is suitable to receive a lamp unit (not shown in detail) as shown in FIG. 8 having one or more UV-lamps. The shown embodiment offers the advantage of straight-through ventilation of the lamp unit by a ventilation unit (not shown in detail), such that the lamp may be cooled and/or heated to guarantee best performance of sterilizing. Depending on the type of UV-lamp best performance is obtained when the lamp surface is in the range of 100° C. The lamp surface is preferably controlled by a sensor directly attached to the lamp surface and interconnected to a control unit, e.g. by wire or wireless. Lamp temperature may also be determined contactless, e.g. by a IR-sensor. Media enters the sterilizing device by a first main connection piece 6 and leaves by a second main connection unit 7. The connection units 6, 7 in the herein shown embodiment are arranged parallel to each other but may also be arranged in steps of 90° to each other. The second main connection unit 7 is equipped with a flow measuring unit 12 suitable to generate a signal corresponding to the volume of media passing through it. Each of the flanges 2, 3 is equipped with a secondary connection piece 8, 9 which can be used as service openings, e.g. for maintenance reason. The secondary connection pieces 8, 9 can be opened and closed by a tap 71.

Figure 10:
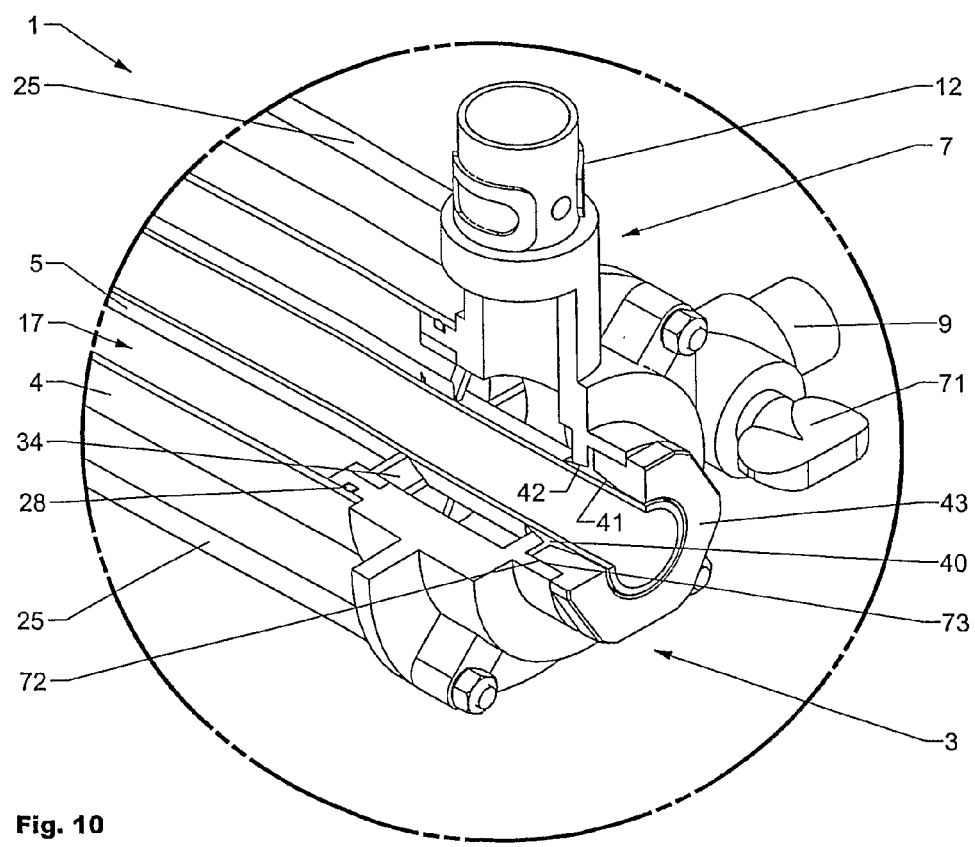
FIG. 10 shows detail D according to FIG. 9.

FIG. 10 shows detail D of FIG. 9. The second flange 3, the inner and the outer tube 4, 5, the second gasket 40 and the coupling nut 43 are partially cut such that it is possible to view the inside of the sterilizing device 1. Between the second flange 3 and the outer tube 4 a first gasket 28 preventing leakage of media which is arranged in the gap 17 between the inner 5 and the outer tube 4. Media to be treated enters the sterilizing device 1 through one of the main connection pieces 6, 7 (see also FIG. 9). After passing through one of the flanges 2, 3, wherein it is already exposed to UV-radiation emitted by a UV-lamp arranged in the inner tube 5, it is then added with turbulence by a vortex unit 34. The vortex unit 34 of the shown embodiment is exchangeable offering the opportunity to be replaced if worn. Downstream it is possible to arranged a conveyer unit (not shown in detail), instead of a vortex unit, to remove at least partially the added turbulence. The vortex unit 34 of the shown embodiment comprises a fan impeller which may be, depending on the field of application, arranged revolving or fixed. The flow measuring device 12 is used to determine the amount of media passing through the sterilizing device. If necessary the sterilizing device may be equipped with a valve gate (not shown in detail) for controlling the flow of the media.

The coupling nut 43 is having an outside thread 72 which corresponds with an inside thread 73 of the flange 3. The second gasket 40 is having two conical shaped surfaces which are corresponding with a first and a second sealing surface 41, 42 of the flange 3 and the coupling nut 43. By driving the coupling 43 into the flange 3 the second gasket 40, which preferably is made out of a deformable, e.g. rubber like material, is deformed radially inward clamping tightly the inner tube 5.

Figures 11, 12:
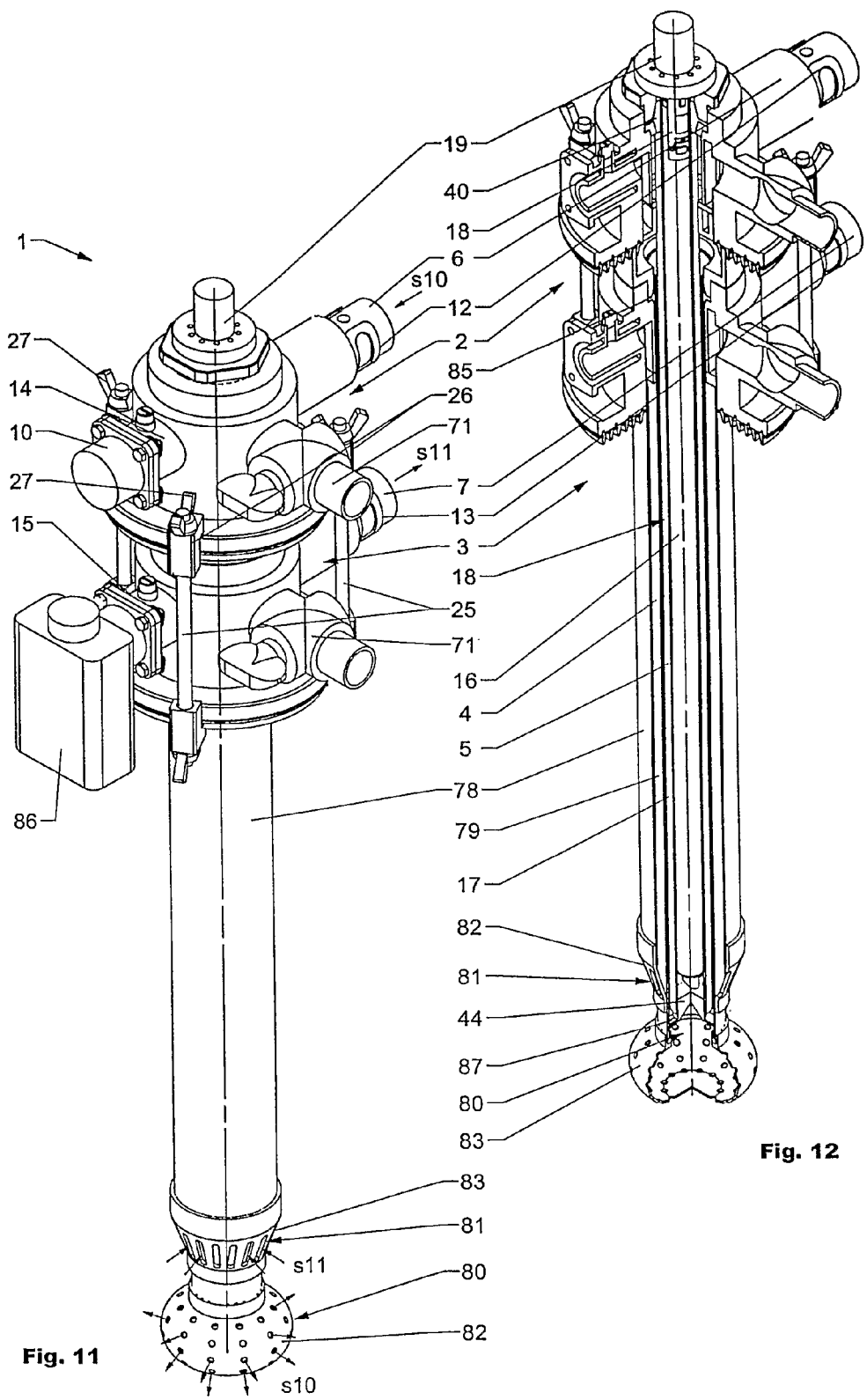
FIG. 11 shows a third embodiment of a sterilizing device in a perspective view.
FIG. 12 shows the sterilizing device in a partially cut view.

FIG. 11 shows a third embodiment of a sterilizing device 1 and FIG. 12 shows the sterilizing device according to FIG. 11 partially cut offering a view at the inside. This embodiment is suitable to be used for water storage, e.g. in stationary water tanks, tanker trucks or water bags. The sterilizing device 1 is inserted e.g. into a filling hole of a tank resting on the rim of the filling hole (not shown in detail), whereby the intake and outlets 80, 81 of the sterilizing device 1 are immersed into the liquid. The fluid pumped into the tank by passing through the second main connection 6 and drained by the first main connection piece 7. In both cases the fluid passes through the first and the second flanges 2, 3 in general according to the flow paths as described in accordance with FIG. 6.

As it can be seen the interface flange 15 of the second flange 3 is equipped with a filter unit 86 through which the fluid passes while being drained. The amount of volume is measured by flow measuring device 13. The interface flange 15 of the first flange 2 is equipped with a valve gate 10 to control the flow through the sterilizing device 1. Alternatively or in addition further filter units and/or valve gates may be arranged. The flanges comprise here a tap 71 which may be used e.g. for maintenance reason. Depending on the filed of application flanges having no interface flange and/or tap may be foreseen. The inner and the outer tube are preferably made both of a material which is transparent for UV-radiation. This offers the opportunity that the fluid entering and the fluid exiting through the sterilizing device 1 is treated by UV-radiation emitted by the lamp 16.

Additionally to or instead of a variety of the filter units 86 the device may be provided with a preferably integrated lasting effect device to improve the action of the filter unit. The lasting effect device which may be used is the one commercialized under the trademark Diacell™ by the Swiss company ADAMANT. The lasting effect may be obtained by the controlled addition of chlorine or any other product having similar effect.

The first and the second flange 2, 3 are arranged next to each other at the upper end of a jacket pipe 78. The jacket pipe 78 is arranged concentrically to the inner and the outer tube 4, 5. Between the inner and the outer tube 4, 5 a first gap 17 and between the jacket pipe 78 and the outer tube 4 a second gap 79 is arranged. The first gap 17 is forming a connection between a first intake/outlet 80 at the lower end of the outer tube 4 and the first main connection piece 6 of the first flange 2. The second gap 79 is forming a connection between a second intake/outlet 81 at the lower end of the jacket pipe 78 and the second main connection piece 7 of the second flange 3. The first and the second intake/outlet 80, 81 are in the present embodiment each covered by a screen 82, 83 which simultaneously acts as a spacer between the outer tube 4 and the jacket pipe 78. A typical flow path of the fluid through the screens 82, 83 is indicated by arrows s10 and s11. In the inner tube a lamp unit 18, a UV-lamp 16 and a control/bulkhead unit 19 are arranged. These units are explained in detail according to FIGS. 7 and 8. The main connection pieces 6, 7 of each flange 2, 3 is equipped with a flow measuring 12, 13 to measure the amount of fluid passing through each of the main connection pieces 6, 7. The first and the second flange 2, 3 are in general similar to each other and are, due to their modular setup also suitable e.g. to be used with a device as described in accordance with FIGS. 1 and 2. Between the first and the second flange 2, 3 a spacer unit 84 is arranged which interconnects the first and the second flange 2, 3. Three tie rods 25 with clamps 26 and clamping screws 27 are holding the first and the second flange 2, 3 together. The inner tube 5 is fixed within the first flange 2 by a second gasket 40 and the outer tube 4 is fixed within the second flange 3 by a third gasket 85. A first gasket 28 is clamped between the first flange 2 and the spacer unit 84. At the opposite end of the spacer unit 84 the third gasket is clamped between the second flange 3 and the spacer unit 84. The second and the third gaskets 40, 85 are made such that they are easily adoptable to inner tubes having different diameters.

The inner tube 5 is hold at the upper end by the second gasket 40 and the coupling nut 43. At the opposite end the inner tube is tightly sealed by the plug 44 which extends into a fan impeller 87 which is serving in this embodiment as a spacer between the inner and the outer tube 4, 5. The plug 44 and the fan impeller 87 are preferably made as two separable parts such that the inner tube 5 and the plug 44 can be pulled out of the sterilizing device 1 after releasing the coupling nut 43.

The sterilizing device 1 as shown offers a modular setup being adoptable to different fields of application. E.g. it is possible to easily adopt the size and the length of the tubes 4, 5, 78 such that the device can be used with different tanks. If applicable each or several components of the sterilizing device 1 can be marked by tags, preferably RFID-tags interconnectable with a control unit, such that false assembly can be avoided. The tags may be equipped with sensors measuring suitable to different parameters of the system and the environment. At least one of the flange preferably comprises a control unit (not shown in detail) suitable to control the device and the sterilizing process.

Figure 13:
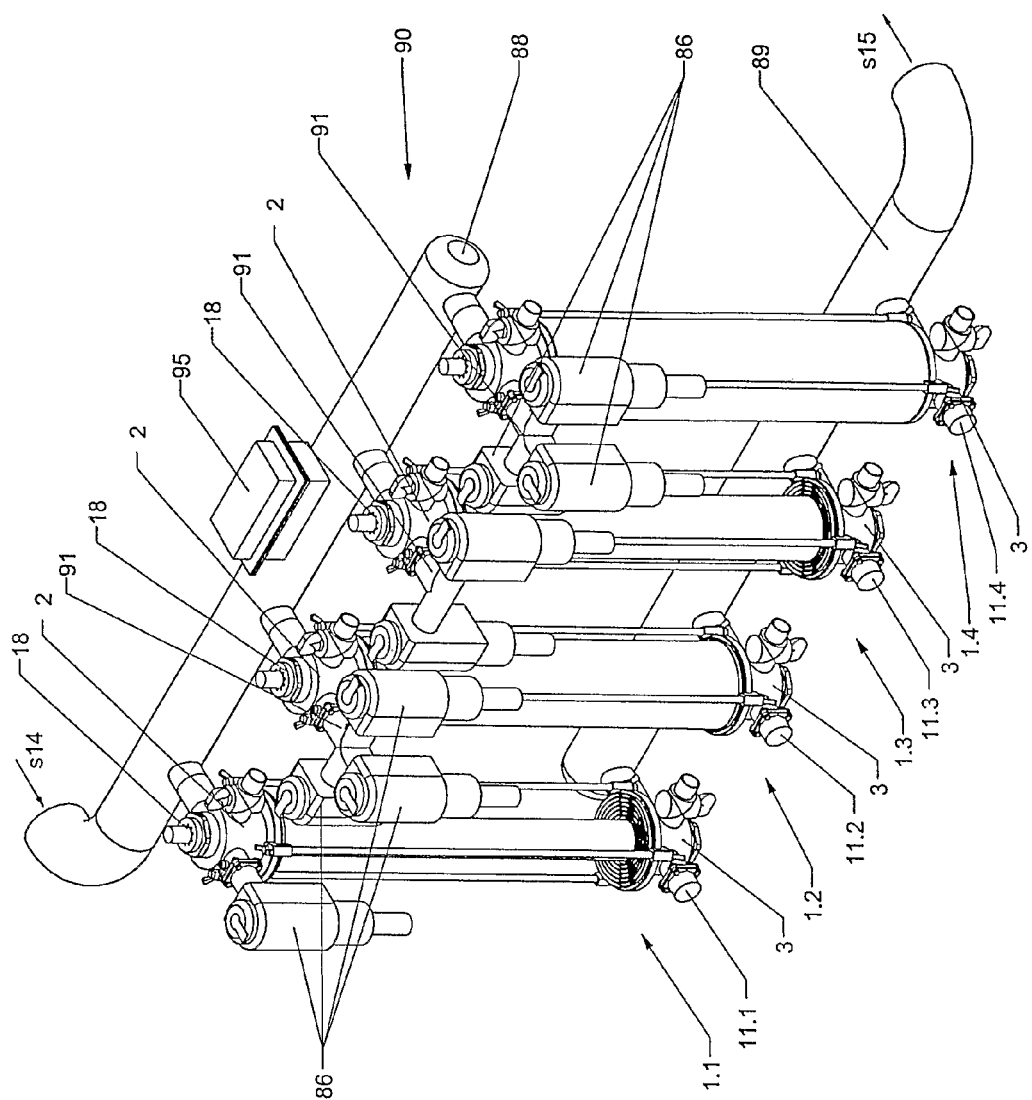
FIG. 13 shows a rack comprising four sterilizing devices.

FIG. 13 is showing a rack 90 with four sterilizing devices 1.1, 1.2, 1.3, 1.4 as it would be appropriate e.g. for treatment of water in a village or a waterworks of a city. As it can be seen the four sterilizing devices 1.1, 1.2, 1.3, 1.4 are arranged parallel to each other sharing a common supply 88 (one or several sources) and a common drainage 89 (both shown only partially). The flow of the water is indicated schematically by arrows s14 and s15. The setup is designed to be able to handle different amounts of water, depending on the present need, by activating and deactivating each sterilizing device by valve gates 11.1, 11.2, 11.3, 11.4 which are interconnected downstream close to the outlet at the second flange 3 of each device. By this arrangement it can be prevented that in case of emergency, e.g. when the inner tube of a device is broken, the device may be deactivated immediately.

E.g. during night time, when only a small amount of water is needed only the first sterilizing device 1.1, having the smallest sterilizing performance, is active. Towards morning a second and a third sterilizing device 1.2, 1.3 may be ignited to handle the occurring peak of consumption. A fourth sterilizing device 1.4 is installed in reserve, such that in case of damage of one of the other sterilizing devices 1.1, 1.2, 1.3, the rack is not loosing it's functionality.

Each sterilizing device 1.1, 1.2, 1.3, 1.4 of the rack 90 is equipped with at least one filter unit 86 connected by a, in the present embodiment x- or t-shaped, adapter 91 or directly to the interface flange 14 of the first flange 2. The adapters 91, the filter units 86 and the interface flanges 14 are having a coaxially setup for intake and outlet of the fluid to be treated.

As it can be seen the outer and, if desirable, the inner tubes 4, 5 of each sterilizing device 1.1, 1.2, 1.3, 1.4 are having different diameters depending on their performance of sterilization. The setup of the UV-lamps is also chosen depending on the performance of each sterilizing device. Therefore a sterilizing device may be equipped with one or more than one UV-lamp.

A central control unit 95 is arranged closed to the supply 88. Depending on the field of application, the control unit 95 is interconnected by wire or wireless, e.g. by radio frequency, with the lamp sensor units 18 of each sterilizing device 1.1, 1.2, 1.3, 1.4. The control unit 95 in general comprises the main logic circuit for controlling the sterilizing devices 1.1, 1.2, 1.3, 1.4. To not influence the transfer of information wireless, the flanges are preferably made of material which is transparent to radio frequency, plastic. If the base material is coated, care has to taken that the radio frequency is not negatively influenced. The advantages of the shown setup are, beside others, it's modularity, the scalable performance, the reduction in overall energy consumption and the increase in safety.

Figures 14, 15:
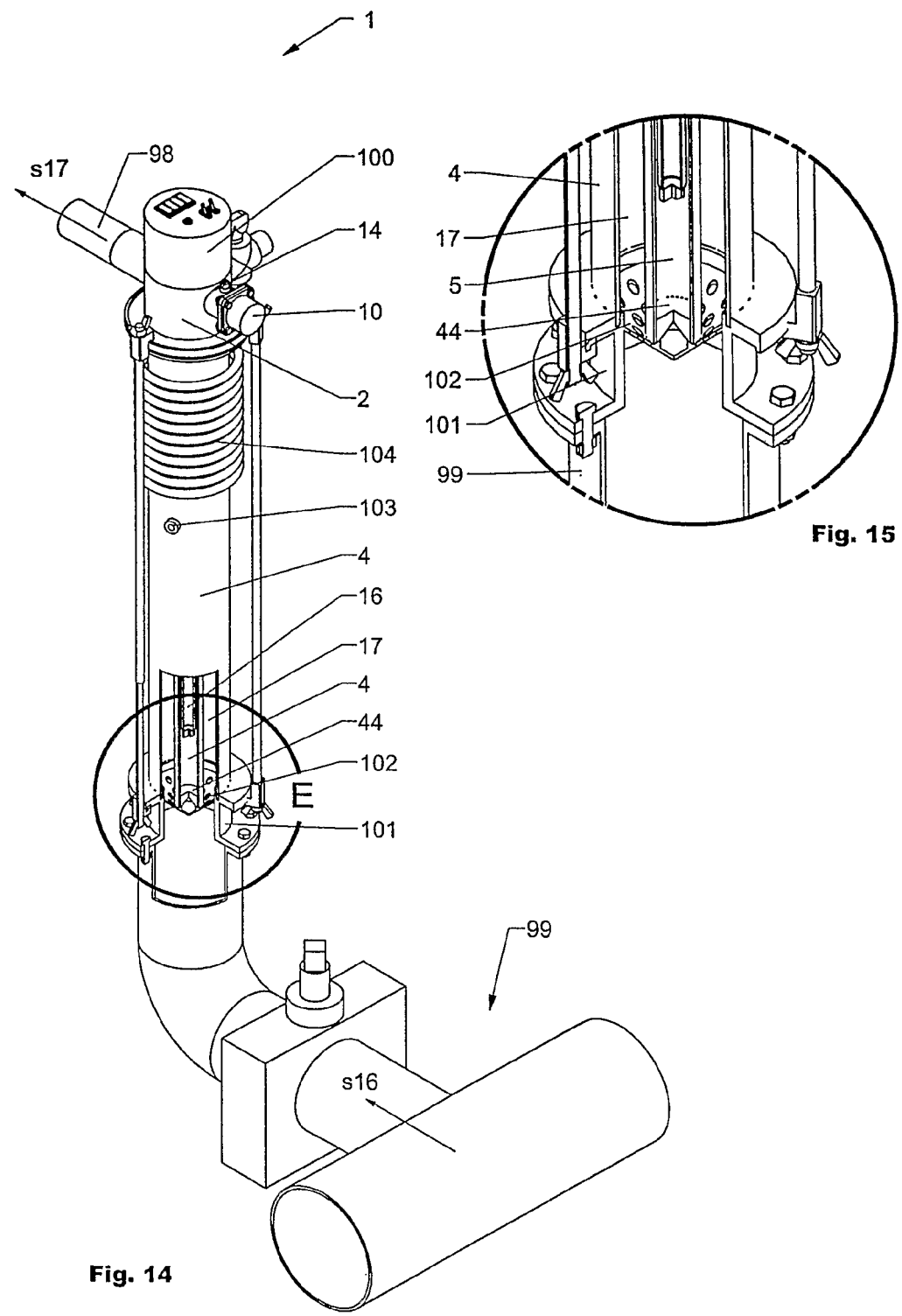
FIG. 14 shows a fourth embodiment of a sterilizing device.
FIG. 15 shows detail E of FIG. 14.

FIG. 14 is showing a further embodiment of a sterilizing device 1 according to the present invention.

FIG. 15 is showing detail E of FIG. 14 in a magnified manner. The herein shown embodiment is an integrated device, e.g. for a building, comprising a sterilizing device 1 and a water meter 100. The sterilizing device 1 typically interconnects an external water supply 99 with a in-house piping system 98 to distribute water. To enable a view at the inside, the sterilizing device 1 is in it's lower area, where it is interconnected to a the external water supply 99, partially cut. The sterilizing device 1 comprises a water meter 100 suitable to determine the volume of water passing through the sterilizing device 1. The water meter 100 may comprise a control unit for controlling the UV-lamp 16 arranged inside the inner tube 5.

The sterilizing device 1 of the present embodiment comprises an upper flange 2 and a therewith connected outer tube 4 which ends at it's lower end in a base flange 101 which is attached to the external water supply 99 with a standardized interface. The base flange 101 comprises a screen 102 to prevent entry of solid material (not shown in detail) from the outside which might damage the sterilizing device 1 and the water meter 100. The base flange 101 may comprise vortex elements to prevent laminar flow in the gap 17. The inner tube 5, which is at it's lower end tightly sealed by a plug 44, rests on a screen 102 and may be pulled out of the flange 2 after releasing a locking device (not shown in detail). A valve gate 10, which is attached to an interface flange 14 of the flange 2, is used to enable or disable to passage of fluid through the sterilizing device 1. A pressure and/or UV-light sensor 103, which is arranged at the sidewall of the outer tube 4, is used to control the sterilizing process of the water in the device 1. In a preferred embodiment the interface flange 14 is used for interconnecting a standardized and sealed water meter (as provided by officials).

The present device further comprises a coil 104 to induce a time-varying magnetic field in the fluid passing through the device 1 to eliminate mineral scale and/or control microbiological populations and/or control corrosion. By inducing the above mentioned fields it is possible to shift the equilibrium chemistry of calcium carbonate to favor formation of stable crystal nuclei in the bulk solution. Thus crystal growth and precipitation can be controlled such that it can be filtered as a loose powder in-stead as a scale on a surface. A suitable filter may be attached further downstream, e.g. to the interface flange 14. The outer tube 4 is made of a material which does not influence the action of the coil 104 negatively.

The water from the external supply 99 enters the sterilizing device 1 by the base flange 101. By the screen 102 solid material of a certain size which might damage the devices is separated. The water stream then enters into the gap 17 between the inner and the outer tube 4, 5 where it is exposed to the UV-radiation of the UV-lamp 16 whereby it is sterilized. The field induced by the coil 104 further prevents scale of the system as explained above. The water enters into the flange 2 wherein it's volume is measured by the water meter 100 and exits then through the valve gate 10 into the piping system 98 e.g. of a building. As it becomes obvious the herein shown device 1 offers the advantage that multiple functions are incorporated in a single device.

The sterilizing device 1 may be equipped with a wireless device, such as an RFID-tag, offering the opportunity to control the sterilizing device 1 and/or the water meter 100 from remote, e.g. from outside the house, by an appropriate control device. Therefore to determine the amount of consumed water the tenants of the house must not be disturbed anymore.

The concept of modularity might have become obvious in that the described embodiments in general all have similar flanges 2, 3.

The invention claimed is:

1. A sterilizing device having a distal end and a proximate end for sterilizing a fluid by UV-radiation, the sterilizing device comprising:
   at least one UV-lamp for emitting UV-radiation that is located between the distal end and the proximate end,
   a lamp tag that is one of attached to and incorporated in the at least one UV-lamp and comprises information regarding the UV-lamp, as
   the lamp tag is interconnected with at least one of a lamp sensor unit and a control unit;
   a first gap is arranged between an inner and an outer tube and a second gap is arranged between a jacket pipe and the outer tube, the first gap defines a first flow path that interconnects a first main connection piece of a first flange and a first intake/outlet and a second gap defines a second flow path that interconnects a second main connection piece of a second flange and a second intake/outlet,
   wherein the at least one UV-lamp is received within the inner tube and a third gap is arranged between a glass cylinder of the UV-lamp and the inner tube,
   the sterilizing device comprises a tank,
   the first main connection piece of the first flange, the first gap, and the first inlet/outlet allow an exchange of water between the tank and the first main connection piece,
   the first intake/outlet couples the first flow path with the tank and the second intake/outlet couples the second flow path with the tank, and
   the first intake/outlet and the second intake/outlet are both located adjacent each other at the distal end of the sterilizing device and the first main connection piece and the second main connection piece are both located adjacent each other at the proximal end of the sterilizing device, and the first flow path being independent of the second flow path.

2. The sterilizing device according to claim 1, wherein the sterilizing device is provided with a fluid quality monitoring sensor, the fluid quality monitoring sensor is either mounted on the first main connection piece or the first flange.

3. The sterilizing device according to claim 1, wherein the sterilizing device further comprises an additional ultrasonic reactor provided for destroying at least one of contaminants, bacteria and microbes.

4. The sterilizing device according to claim 3, wherein the additional ultrasonic reactor is located outside of the outer tube, and is either attached to an outer surface of the outer tube or inline to the outer tube.

5. The sterilizing device according to claim 3, wherein the additional ultrasonic reactor is located inside of the outer tube.

6. The sterilizing device according to claim 3, wherein the additional ultrasonic reactor has one of a ring shape, a cylindrical shape and a conical shape.

7. The sterilizing device according to claim 1, wherein the lamp tag comprises at least one sensor for measuring at least one of a surface temperature of the UV-lamp and a working life of the UV-lamp.

8. The sterilizing device according to claim 1, wherein the lamp tag comprises a memory for storing information about at least one of a specification, a condition of the UV-lamp and wear of the UV-lamp, and the lamp sensor unit is located within the inner tube radially between the UV-lamp and the inner tube.

9. The sterilizing device according claim 1, wherein the lamp tag is an RFID-tag wirelessly interconnected with the control unit and comprises identification information of the UV-lamp such that the control unit recognizes the identification of the UV-lamp so as to inhibit insertion of an incompatible lamp into the device.

10. The sterilizing device according to claim 1, wherein the inner tube is made of a material transparent to UV-radiation, a vortex unit is arranged around the inner tube which forms a helical flow of the fluid around the inner tube.

11. The sterilizing device according to claim 1, wherein the first flange comprises an interface flange for interconnection of at least one of a filter unit, a valve gate, a sensor unit and a water meter.

12. The sterilizing device according to claim 1, wherein the first flange comprises a mechanical fluid treatment system for decomposition of organic and chemical contamination.

13. The sterilizing device according to claim 1, wherein at least one of the first flange and the second flange comprises at least one of an exchangeable vortex and conveyer unit.

14. The sterilizing device according to claim 1, wherein at least one of the first flange and the second flange comprises a flow measuring unit for measuring a volume of fluid passing through the sterilizing device.

15. The sterilizing device according to claim 14, wherein the flow measuring unit comprises first and second coils arranged opposite to each other and first and second electrodes arranged opposite to each other and perpendicular to the first and the second coils.

16. The sterilizing device according to claim 1, wherein at least one of the first flange, the second flange, the inner tube and the outer tube comprise a pressure sensor.

17. The sterilizing device according to claim 1, wherein a sensor unit is arranged at one side of the first gap for measuring at least one of an intensity of UV-radiation passing through the fluid and a temperature of the fluid.

18. The sterilizing device according to claim 1, wherein a lamp sensor unit is arranged between the UV-lamp and the inner tube and comprises at least one of a lamp temperature sensor for measuring a temperature of the at least one UV-lamp, a fluid temperature sensor for measuring at least one of a temperature of the fluid in the gap, and a velocity sensor for measuring velocity of the fluid in the gap.

19. The sterilizing device according to claim 1, wherein the outer tube is clamped between the first flange and the second flange interconnected by tie rods.

20. The sterilizing device according to claim 1, wherein the sterilizing device comprises a coil to induce a time-varying magnetic field in the fluid passing through the sterilizing device to at least one of eliminate mineral scale, control microbiological populations, and control corrosion.

21. The sterilizing device according to claim 20, wherein the coil is arranged concentrically to one of the inner and the outer tubes.

22. The sterilizing device according to claim 1, wherein the lamp tag comprises at least one sensor for measuring the surface temperature of the UV-lamp.

23. The sterilization device according to claim 22, comprising a cooling unit for the UV-lamp which is controlled by the control unit and adapted to control the UV-lamp depending upon the measured temperature.

24. The sterilization device according to claim 23, wherein the cooling unit is adapt to compute the operating life time of the UV-lamp on a basis of the measured temperature.

25. The sterilization device according to claim 23, wherein the cooling unit is adapt to compute the operating life time of the UV-lamp on a basis of the measured temperature and information about the UV-lamp stored in the lamp tag.

26. The sterilization device according to claim 1, wherein the glass cylinder is a replacable bulb of the UV-lamp.

* * * * *